United States Patent [19]
Jubin, Jr.

[11] Patent Number: 5,149,885
[45] Date of Patent: Sep. 22, 1992

[54] OXIDATION OF ISOBUTANE TO TERTIARY BUTYL HYDROPEROXIDE

[75] Inventor: John C. Jubin, Jr., West Chester, Pa.

[73] Assignee: Arco Chemical Technology, L.P., Wilmington, Del.

[21] Appl. No.: 839,983

[22] Filed: Feb. 20, 1992

[51] Int. Cl.$^5$ .......................... C07C 409/04
[52] U.S. Cl. .................... 568/571; 568/564; 568/569
[58] Field of Search ............... 568/565, 569, 571, 570, 568/564

[56] References Cited

U.S. PATENT DOCUMENTS

| | | | |
|---|---|---|---|
| 2,845,461 | 7/1958 | Winkler et al. | 568/571 |
| 4,263,448 | 4/1981 | Leacock | 568/571 |
| 4,404,406 | 9/1983 | Lutz et al. | 568/571 |
| 4,408,081 | 10/1983 | Foster | 568/571 |
| 4,408,082 | 10/1983 | Baumgarter | 568/571 |

OTHER PUBLICATIONS

Winkler et al, "Ind. & Eng. Chem." vol. 53(8) pp. 655–658.

Primary Examiner—Werren B. Lone
Attorney, Agent, or Firm—William C. Long

[57] ABSTRACT

The present invention relates to the oxidation of isobutane to TBHP wherein the oxidation exothermic heat of reaction is removed by circulating a portion of the liquid reaction mixture through an indirect heat exchanger and comprises the further feature that the molecular oxygen necessary for the oxidation is introduced by means of sparging into the cooled, circulating liquid reaction mixture.

4 Claims, 1 Drawing Sheet

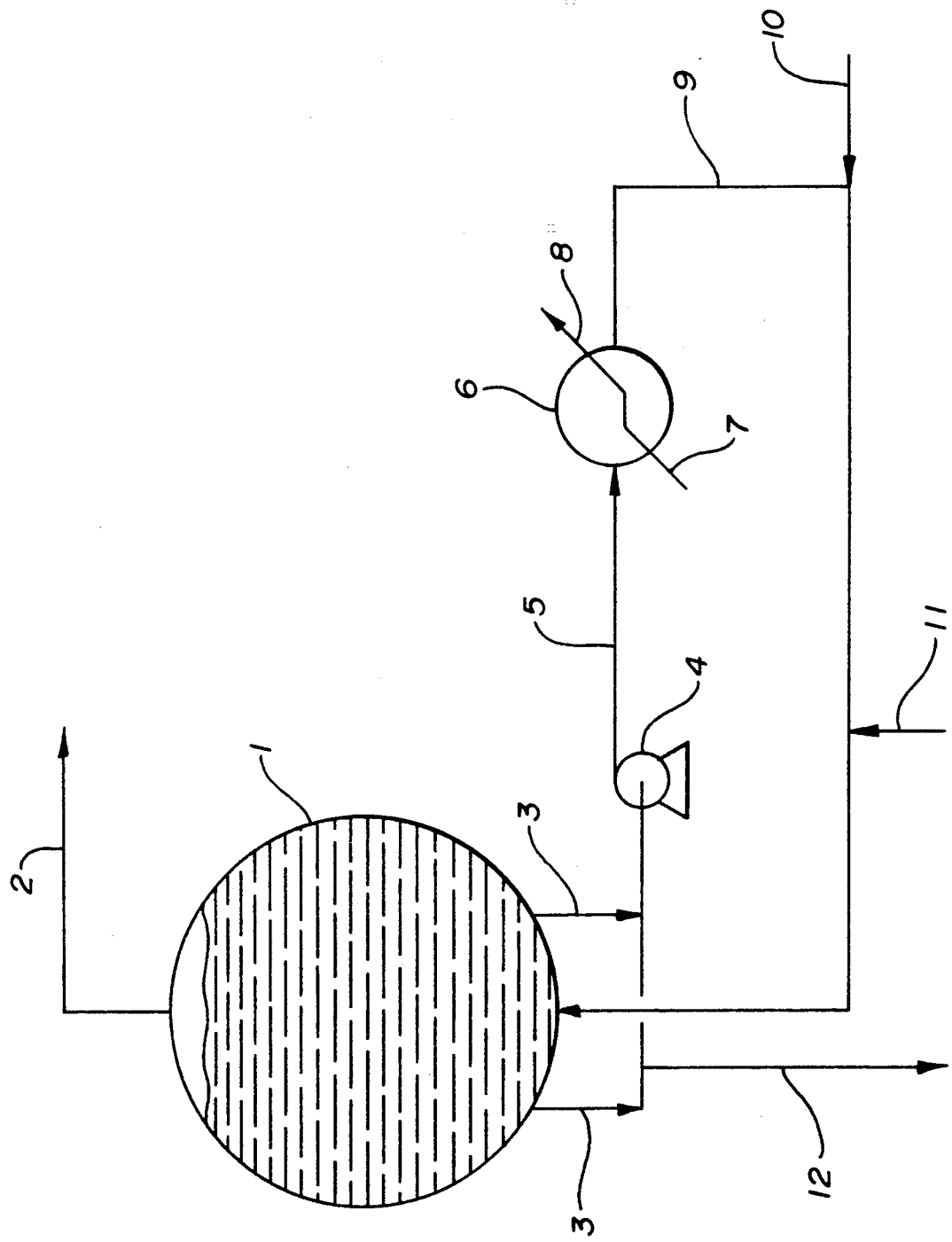

5,149,885

OXIDATION OF ISOBUTANE TO TERTIARY BUTYL HYDROPEROXIDE

BACKGROUND OF THE INVENTION

1. Field of the Invention

The present invention relates to the oxidation of isobutane to tertiary butyl hydroperoxide (TBHP) and to an improved method for carrying out the oxidation.

2. Description of Prior Art

Method are known for the production of TBHP by the molecular oxygen oxidation of isobutane at elevated temperature and pressure. In this regard, attention is drawn to U.S. Pat. No. 2,845,461 of Winkler, et al., to U.S. Pat. No. 3,478,108 of Grane and to U.S. Pat. No. 4,408,081 of Foster, et al.

There are problems associated with the isobutane oxidation. The reaction is exothermic, and the substantial exotherm must be removed during continuous operation. Methods suggested for the heat removal include vaporization of components of the reaction mixture, external condensation and return of condensate to the reaction zone. Alternatively, the provision of cooling coils within the reaction zone is an alternative method for removing the heat of reaction.

A problem in addition to heat removal has been the avoidance of hazardous mixtures upon introducing isobutane and oxygen into the reaction zone. Special equipment and procedures have been required.

In accordance with the present invention, a simplified system is provided whereby the heat of reaction of the isobutane oxidation is conveniently removed, reactor design is greatly simplified, and oxygen is introduced with improved ease and safety.

BRIEF DESCRIPTION OF THE INVENTION

In practice of the invention, isobutane is reacted in the liquid phase at known reaction conditions to form TBHP. A significant amount of tertiary butyl alcohol (TBA) is also formed as is well known. The heat of reaction is removed by circulating a portion of the liquid reaction mixture through an indirect heat exchanger located external of the reactor and then after appropriate cooling, the cooled liquid is returned to the reaction zone. As a special feature, the oxygen necessary for the isobutane oxidation is injected into the cooled, circulating liquid reaction mixture and is carried with the cooled liquid into the reaction zone. In this way, hazards associated with the formation of flammable vapor mixtures of isobutane and oxygen are substantially avoided, equipment construction and operation are simplified and the heat of reaction is effectively removed.

DESCRIPTION OF THE DRAWING

The accompanying drawing illustrates in schematic form practice of the invention.

DETAILED DESCRIPTION

The invention can best be described with reference to the accompanying drawing. Referring to the drawing, isobutane is reacted with oxygen in reactor 1 to produce TBHP along with TBA. Reactor 1 is preferably a substantially liquid filled reactor, suitably of a spherical shape although other shapes can be employed.

The isobutane oxidation reaction conditions in oxidation reactor 1 are those which are normally used for this reaction as described, for example, in Winkler, et al. U.S. Pat. No. 2,845,461. Generally, reaction temperatures in the range of 100° C. to 200° C., preferably 120° C. to 150° C. are employed. Pressures in the range of 300 to 500 psig, preferably 400 to 450 psig are employed. Residence times in the oxidation zone of 3 to 15 hours, preferably 5 to 10 hours are suitable.

It is preferred to use oxygen as the oxidant, although the use of oxygen in admixture with minor amounts of an inert gas such as nitrogen can be used. A vent gas is removed via line 2 to prevent inerts build-up and unreacted isobutane can be recovered therefrom and recycled (not shown).

As shown in the drawing, it is especially advantageous to operate with reactor 1 substantially full of the liquid reaction mixture, i.e. preferably at least 80 wt. % full and most preferably at least 95 wt. % full. In accordance with the invention, the exothermic heat of reaction is removed by cooling a circulating stream of liquid reaction mixture. Specifically, a portion of the liquid reaction mixture is withdrawn from reactor 1 through line 3 and is pumped via pump 4 and line 5 to indirect heat exchanger 6. As depicted in the drawing, exchanger 6 is a steam boiler with the boiler feed water introduced by means of line 7 and the generated steam recovered by means of line 8.

It is especially advantageous to practice the invention with very high circulation rates of the removed liquid reaction mixture whereby the reaction exotherm can be removed with a minimum temperature drop of the circulating liquid. It is especially preferred that the circulation rate be maintained such that the circulating liquid is reduced in temperature by less than 50° F. and preferably less than about 25° F.

The cooled, circulating liquid reaction mixture passes from exchanger 6 via line 9 and is returned to reactor 1. As a critical feature of the present invention, the oxygen fed to reactor 1 is sparged into the cooled circulating reaction mixture via line 10 and passes with this circulating mixture to reactor 1. By means of this sparged injection, the oxygen is rapidly dissolved in the reaction liquid, with any undissolved oxygen being maintained in the form of small bubbles due to the rapid motion and agitation of the circulating liquid.

In an especially preferred practice, the feed isobutane is also introduced into the cooled, circulating reaction line 11 and passes in admixture with the circulating liquid and the injected oxygen to reactor 1 wherein the oxidation of the isobutane to TBHP takes place. The isobutane can also be sparged into the circulating liquid as a preferred but not essential method of introduction.

The net reaction product from reactor 1 comprised of TBHP, TBA and unreacted isobutane is removed via lines 3 and 12 to subsequent treatment steps wherein by known procedures unreacted isobutane is separated from the oxidate.

Through practice of the invention, optimum reactor configurations, notably a spherical shape, can be employed. The exothermic reaction heat is conveniently removed by indirect heat exchange with the circulating liquid reaction mixture and valuable steam can thereby be generated and recovered. Additionally, by injecting oxygen reagent directly into the cooled, circulating reaction liquid, problems and hazards associated with he formation of vapor mixtures of isobutane and oxygen are substantially avoided.

EXAMPLE

Referring to FIG. 1, isobutane is continuously oxidized in spherical reactor 1 by reaction with molecular oxygen. Reactor 1 is operated substantially full of liquid and the oxidation conditions maintained therein are 137° C. and 435 psig. Isobutane is fed to reactor 1 by means of line 11 at the rate of 145 M lbs./hr. As shown in the drawing, the isobutane is actually added to the circulating oxidate stream and is carried into oxidation zone 1 with the circulating oxidate to which oxygen has previously been added.

In order to remove the exothermic heat of reaction, liquid oxidate comprised of 62 mol. % isobutane, 15 mol. % TBA, and 20 mol. % TBHP, and 3 mol. % of others is withdrawn from zone 1 by means of line 3 at the rate of 3300 M lbs./hr. The withdrawn oxidate passes via pump 4 and line 5 to indirect heat exchanger 6 wherein the circulating oxidate is cooled by indirect heat exchange with boiling water which is introduced via line 7. The temperature of the circulating oxidate is reduced to 125° C. by the indirect heat exchange, and steam which is generated in exchanger 6 is removed via line 8. The circulating oxidate passes from heat exchanger 6 via line 9 back to reaction zone 1. The oxygen required for the conversion of isobutane is introduced at the rate of 22.7 M lbs./hr. via line 10 and is sparged into the circulating oxidate in line 9. Conveniently, the oxygen is injected by appropriate sparging means into the circulating liquid in the form of fine bubbles. Oxygen having a purity of 99.6% by volume is employed; the remainder of the oxygen feed comprises inerts.

A vent gas is removed from the oxidation zone 1 via line 2 in order to purge inerts which are associated with the oxygen. The composition of the vent gas is 1 mol. % oxygen, 82 mol. % isobutane, 5 mol. % TBHP/TBA and 12 mol. % inerts.

Net product oxidate having the same composition as the circulating oxidate is removed via lines 3 and 12 at the rate of 164 M lbs./hr. and comprises the product of the oxidation reaction.

I claim:

1. In a process for the molecular oxygen oxidation of isobutane to TBHP wherein isobutane and molecular oxygen are fed to a reaction zone and reacted therein in the liquid phase at conditions effective to form TBHP, the improvement which comprises continuously removing a liquid reaction mixture stream from the reaction zone, cooling said stream by indirect heat exchange with a heat transfer fluid thereby to remove the reaction exotherm, returning the cooled reaction mixture to the reaction zone, and injecting the molecular oxygen feed to the reaction into the cooled reaction mixture prior to the return thereof to the reaction zone.

2. The process of claim 1 wherein feed isobutane to the reaction zone is also injected into the cooled reaction mixture after the molecular oxygen injection.

3. The process of claim 1 wherein the reaction zone is substantially completely filled with reaction liquid.

4. The process of claim 1 wherein the reaction zone is spherical.

* * * * *